United States Patent [19]

Rüger et al.

[11] Patent Number: 5,116,835
[45] Date of Patent: May 26, 1992

[54] ENZYME-INHIBITING UREA DERIVATIVES OF DIPEPTIDES, A PROCESS FOR THE PREPARATION THEREOF, AGENTS CONTAINING THESE, AND THE USE THEREOF

[75] Inventors: Wolfgang Rüger, Kelkheim; Hansjörg Urbach; Dieter Ruppert, both of Kronberg/Taunus; Bernward Schölkens, Kelkheim, all of Fed. Rep. of Germany

[73] Assignee: Hoechst Aktiengesellschaft, Frankfurt am Main, Fed. Rep. of Germany

[21] Appl. No.: 447,414

[22] Filed: Dec. 7, 1989

[30] Foreign Application Priority Data

Dec. 9, 1988 [DE] Fed. Rep. of Germany ....... 3841520

[51] Int. Cl.$^5$ .................. A61K 31/55; A61K 31/535; C07D 243/08; C07D 417/00
[52] U.S. Cl. ................... 514/218; 514/227.8; 514/235.8; 514/236.5; 514/235.5; 514/255; 514/256; 514/316; 514/318; 514/326; 514/341; 514/343; 514/365; 514/397; 540/575; 540/596; 540/597; 540/598; 540/601; 540/602; 540/603; 544/60; 544/121; 544/129; 544/132; 544/133; 544/141; 544/295; 544/333; 544/335; 544/357; 544/360; 544/364; 544/365; 544/370; 544/371; 544/372; 544/374; 544/379; 546/187; 546/189; 546/193; 546/194; 546/208; 546/209; 546/210; 546/211; 546/278; 546/281; 548/336
[58] Field of Search ............ 514/19, 252, 227.8, 514/235.8, 236.5, 235.5, 255, 256, 316, 318, 326, 341, 343, 365, 397, 218; 530/331; 544/360, 60, 121, 129, 132, 133, 141, 295, 333, 335, 357, 364, 365, 370, 371, 372, 374, 379; 260/998.2; 546/187, 189, 193, 194, 208, 209, 210, 211, 278, 281; 548/336

[56] References Cited

U.S. PATENT DOCUMENTS 4,725,583  2/1988  Luly et al. .................. 530/331
4,812,555  3/1989  Raddatz et al. ............. 530/330
4,840,935  6/1989  Wagnon et al. .............. 530/330
4,855,286  8/1989  Wagner ...................... 548/495

FOREIGN PATENT DOCUMENTS 0283970  9/1988  European Pat. Off. .

OTHER PUBLICATIONS

Haher, "Renin Inhibitors", J. Cardiovascular Phermacology, 10 Supp. 7 (S54–58) 1987.
Bolis, "Renis Inhibitors & Dipeptids of Angiotensinogen" J. Med. Chem. 1987, 30, 1729–1737.
J. Med. Chem. 1988, 31, 2277–2288 Burger, "Med. Chem." 2nd edition, Interscience Publisher Jun. 27, 1960. NY p. 565.
Denkewalter, "Program in Drug Research" vol. 10, 1966 p. 510.

*Primary Examiner*—Lester L. Lee
*Assistant Examiner*—Christina Chan
*Attorney, Agent, or Firm*—Finnegan, Henderson, Farabow, Garrett, and Dunner

[57] ABSTRACT

Enzyme-inhibiting urea derivatives of dipeptides, a process for the preparation thereof, agents containing these, and the use thereof.

The present invention relates to compounds of the formula I

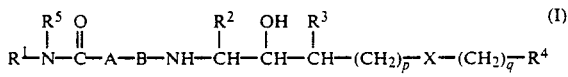

in which
A and B denote, indpendently of one another, an amino acid,
X as desired can be absent or represents —O—, —S—, —CF$_2$—, —CO— or —CHR$^8$,
p and q denote, independently of one another, 0, 1, 2, 3 or 4, and
R$^1$ to R$^4$ are defined in the description, as well as the salts thereof.

The invention furthermore relates to a process for the preparation of the compounds of the formula I and to the use thereof as medicines.

3 Claims, No Drawings

ENZYME-INHIBITING UREA DERIVATIVES OF DIPEPTIDES, A PROCESS FOR THE PREPARATION THEREOF, AGENTS CONTAINING THESE, AND THE USE THEREOF

DESCRIPTION

EP-A255,082 discloses di- and tripeptide derivatives which may carry on the N-terminus inter alia a monosubstituted urea fragment and which have a renin-inhibitory action.

EP-A283,970 describes urea derivatives of dipeptides having a renin-inhibitory action.

It has now been found, surprisingly, that disubstituted urea derivatives of dipeptides which differ from the compounds disclosed in EP-A255,082 by an additional substituent on the N-terminal nitrogen atom and from the compounds described in EP-A283,970 by the nature of the substituent R, highly effectively inhibit in vitro and in vivo the enzyme renin and retroviral aspartyl proteases.

The present invention relates to compounds of the formula I

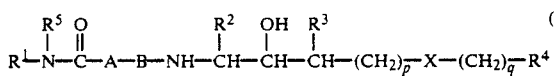

in which $R^1$ denotes hydrogen, $(C_1-C_{10})$-alkyl which is optionally singly or doubly unsaturated and which is optionally substituted by up to 3 identical or different radicals from the series comprising hydroxyl, $(C_1-C_7)$-alkoxy, $(C_1-C_7)$-alkanoyloxy, carboxyl, $(C_1-C_7)$-alkoxycarbonyl, Cl, Br, amino, $(C_1-C_7)$-alkylamino, di-$(C_1-C_7)$-alkylamino, $(C_1-C_5)$-alkoxycarbonylamino, $(C_7C_{15})$-aralkoxycarbonylamino and 9-fluorenylmethyloxycarbonylamino, or $(C_3-C_8)$-cycloalkyl, $(C_3-C_8)$-cycloalkyl-$(C_1-C_6)$-alkyl, $(C_8-C_{14})$-aryl which is optionally substituted by one or two identical or different radicals from the series comprising F, Cl, Br, I, hydroxyl, $(C_1-C_7)$-alkoxy, $(C_1-C_7)$-alkyl, $(C_1-C_7)$-alkoxycarbonyl, amino, anilino which is optionally substituted by up to 2 halogen, and trifluoromethyl; $(C_8-C_{14})$-aryl-$(C_1-C_6)$-alkyl in which the aryl moiety is optionally substituted by one or two identical or different radicals from the series comprising F, Cl, Br, I, hydroxyl, $(C_1-C_7)$-alkoxy, $(C_1-C_7)$-alkyl, $(C_1-C_7)$-alkoxycarbonyl, amino, $(C_1-C_7)$-alkylamino, di-$(C_1-C_7)$-alkylamino, carboxyl, carboxymethoxy, amino-$(C_1-C_7)$-alkyl, $(C_1-C_7)$-alkylamino-$(C_1-C_7)$-alkyl, di-$(C_1-C_7)$-alkylamino-$(C_1-C_7)$-alkyl, $(C_1-C_7)$-alkoxycarbonylmethoxy, carbamoyl, sulfamoyl, $(C_1-C_7)$-alkoxysulfonyl, sulfo- and guanidinomethyl, or represents the radical of a 3- to 8-membered monocyclic or 7- to 13-membered bicyclic heterocycle which has at least 1 carbon atom, 1–4 nitrogen atoms and/or 1 sulfur or oxygen atom also as ring members and is optionally substituted by one, two or three identical or different radicals from the series comprising F, Cl, Br, hydroxyl, $(C_1-C_7)$-alkoxy, $(C_1-C_7)$-alkyl, $(C_1-C_7)$-alkoxycarbonyl, amino or trifluoromethyl, A denotes a radical, which is linked N-terminal via $-NR^6$with $-CO-$ and C-terminal via $-CO-$ with B, of a natural or unnatural amino acid from the series comprising phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine,1-naphthylalanine,2-naphthylalanine, 4-nitrophenylalanine, norvaline, β-2-benzo[b]thienylalanine, β-3-benzo[b]thienylalanine, 2-fluorophenylalanine, 3-fluorophenylalanine, 4-fluorophenylalanine, norleucine, cysteine, S-methyl-cysteine, 1,2,3,4-tetrahydroisoquinoline-3-carboxylic acid, homophenylalanine, DOPA, O-dimethyl-DOPA,2-amino-4-(2-thienyl)-butyric acid, benzodioxol-5-yl-alanine, N-methyl-histidine, 2-amino-4-(3-thienyl)butyric acid, 3-(2-thienyl)-serine, (Z)-dehydrophenylalanine,(E)-dehydrophenylalanine, (1,3-dioxolan-2-yl)alanine, N-pyrrolylalanine, (1-, 3- or 4-pyrazolyl)alanine, 4-(thiazolyl)alanine, (2-, 4- or 5-pyrimidyl)alanine, cyclopentylglycine, tert.butylglycine or phenylserine and $R^6$ denotes hydrogen, $(C_1-C_6)$-alkyl, formyl, $(C_1-C_6)$-alkoxycarbonyl or benzyloxycarbonyl, B denotes a radical, which is linked N-terminal via $-NR^7-$ with A and C-terminal via $-CO-$ with

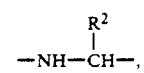

of a natural or unnatural amino acid as defined for A, and $R^7$ denotes hydrogen, $(C_1-C_6)$-alkyl, formyl, $(C_1-C_8)$-alkoxycarbonyl or benzyloxycarbonyl, $R^2$ denotes hydrogen, $(C_1-C_{10})$-alkyl, $(C_4-C_7)$-cycloalkyl, $(C_4-C_7)$-cycloalkyl-$(C_1-C_6)$-alkyl, $(C_6-C_{14})$-aryl, $(C_6-C_{14})$-aryl-$(C_1-C_6)$-alkyl or (heterocyclyl)-$(C_1-C_6)$-alkyl, where the heterocycle has 4–7 ring members, 1 or 2 of which are sulfur and/or oxygen atoms, $R^3$ denotes hydrogen, $(C_1-C_{10})$-alkyl, $(C_6-C_{14})$-aryl or $(C_6-C_{14})$-aryl-$(C_1-C_6)$-alkyl, X as desired can be absent or represents $-O-$, $-S-$, $-CF_2-$, $-CO-$ or $-CHR^8-$, in which $R^8$ denotes hydrogen, $(C_1-C_7)$-alkyl, $(C_1-C_5)$-alkoxy, $(C_1-C_5)$-alkylthio, $(C_1-C_5)$-alkylamino, $-OH$, $-N_3$, $-F$, $-Cl$, $-Br$ or $-I$, $R^4$ denotes $-OH$, $-NH_2$ or heteroaryl which can also be partially or completely hydrogenated and which is optionally substituted by one, two or three identical or different radicals from the series comprising F, Cl, Br, hydroxyl, $(C_1-C_7)$-alkoxy, $(C_1-C_7)$-alkyl, $(C_1-C_7)$-alkoxycarbonyl, amino or trifluoromethyl, p and q denote, independently of one another, 0, 1, 2, 3 or 4, $R^5$ has the same meaning as $R^1$ or else forms, together with $R^1$ and the nitrogen atom connecting them, a three- to eight-membered monocycle or a seven- to thirteen-membered bicycle which has at least 1 carbon atom, 1–4 nitrogen atoms and/or 1 sulfur or oxygen atom as ring members and which can optionally be substituted by one, two or three identical or different radicals from the series comprising $(C_1-C_6)$-alkyl, hydroxyl, hydroxy-$(C_1-C_6)$-alkyl, $(C_1-C_6)$-alkoxy, $(C_1-C_6)$-alkoxy-$(C_1-C_6)$-alkyl, carboxyl, carboxy-$(C_1-C_6)$-alkyl, $(C_1-C_6)$-alkoxycarbonyl, $(C_1-C_6)$-alkoxycarbonyl-$(C_1-C_6)$-alkyl, halogen, amino, amino-$(C_1-C_6)$-alkyl, $(C_1-C_6)$-alkylamino, $(C_1-C_6)$-alkylamino-$(C_1-C_6)$-alkyl, di-$(C_1-C_6)$-alkylamino or di-$(C_1-C_6)$-alkylamino-$(C_1-C_6)$-alkyl, as well as the physiologically tolerated salts thereof.

The centers of chirality in the compounds of the formula I can have the R or S or R,S configuration.

Alkyl can be straight-chain or branched. A corresponding statement applies to radicals derived therefrom such as, for example, alkoxy, alkylthio, alkylamino, dialkylamino, alkanoyl and aralkyl.

Cycloalkyl also means alkyl-substituted radicals such as, for example, 4-methylcyclohexyl or 2,3-dimethylcyclopentyl.

$(C_6-C_{14})$-aryl is, for example, phenyl, naphthyl, biphenylyl or fluorenyl; phenyl is preferred. A corresponding statement applies to radicals derived therefrom such as, for example, aralkyl. Aralkyl means an unsubstituted or substituted $(C_6-C_{14})$-aryl radical which is linked to $(C_1-C_6)$-alkyl, such as, for example, benzyl, α- and β-naphthylmethyl, halobenzyl and alkoxybenzyl.

Heteroaryl, heterocycle and a radical of a 3- to 8-membered monocyclic or 7- to 13-membered bicyclic heterocycle having at least 1 carbon atom, 1-4 nitrogen atoms and/or 1 sulfur or oxygen atom as ring members means radicals of heteroaromatics as defined, for example, in Katritzky, Lagowski, Chemistry of the Heterocycles, Berlin, Heidelberg 1968. The heteroaromatic radical can be substituted by one, two or three, preferably one or two, identical or different radicals from the series comprising F, Cl, Br, hydroxyl, $(C_1-C_7)$-alkoxy, $(C_1-C_7)$-alkyl, $(C_1-C_7)$-alkoxycarbonyl, amino or trifluoromethyl. Examples of monocyclic heteroaromatics are thiophene, furan, pyrrole, imidazole, pyrazole, pyridine, pyrazine, pyrimidine, pyridazine, 1,2,4-triazole, thiazole, tetrazole, isothiazole, oxazole and isoxazole. Examples of bicyclic heteroaromatics are benzothiophene, benzofuran, indole, isoindole, indazole, benzimidazole, quinoline, isoquinoline, phthalazine, quinoxaline, quinazoline and cinnoline. A corresponding statement applies to the radicals derived from heteroaryl, such as, for example, completely or partially hydrogenated heteroaryl-alkyl.

The amino acids A and B in formula I are linked together by an amide linkage. They are natural or unnatural α-amino acids of the L or D or D,L configuration, preferably of the L configuration.

Salts of compounds of the formula I mean, in particular, pharmaceutically utilizable or non-toxic salts.

Salts of these types are formed, for example, from compounds of the formula I which contain acidic groups, for example carboxyl, with alkali metals or alkaline earth metals such as Na, K, Mg and Ca, as well as with physiologically tolerated organic amines such as, for example, triethylamine and tri-(2-hydroxyethyl)-amine. Compounds of the formula I which contain basic groups, for example an amino group or a guanidino group, form salts with inorganic acids such as, for example, hydrochloric acid, sulfuric acid or phosphoric acid and with organic carboxylic or sulfonic acids such as, for example, acetic acid, citric acid, benzoic acid, maleic acid, fumaric acid, tartaric acid and p-toluenesulfonic acid.

Preferred compounds of the formula I are those in which
$R^1$ denotes hydrogen, $(C_1-C_{10})$-alkyl which is optionally substituted by up to three identical or different radicals from the series comprising hydroxyl, $(C_1-C_4)$-alkoxy, $(C_1-C_4)$-alkanoyloxy, carboxyl, $(C_1-C_4)$-alkoxycarbonyl, Cl, Br, amino, $(C_1-C_4)$-alkylamino, di-$(C_1-C_4)$-alkylamino or $(C_1-C_4)$-alkoxycarbonylamino, or $(C_5-C_7)$-cycloalkyl, $(C_6-C_{14})$-aryl which is optionally substituted by one or two identical or different radicals from the series comprising F, Cl, Br, hydroxyl, $(C_1-C_4)$-alkoxy, $(C_1-C_4)$-alkyl, $(C_1-C_4)$-alkoxycarbonyl, amino and trifluoromethyl, or $(C_6-C_{14})$-aryl-$(C_1-C_6)$-alkyl in which the aryl moiety is optionally substituted by one or two identical or different radicals from the series comprising F, Cl, Br, hydroxyl, $(C_1-C_4)$-alkoxy, $(C_1-C_4)$-alkyl, $(C_1-C_4)$-alkoxycarbonyl, amino, $(C_1-C_4)$-alkylamino, di-$(C_1-C_4)$-alkylamino, carboxyl, carboxymethoxy, amino-$(C_1-C_4)$-alkyl, $(C_1-C_4)$-alkylamino-$(C_1-C_4)$-alkyl, di-$(C_1-C_4)$-alkylamino-$(C_1-C_4)$-alkyl, $(C_1-C_4)$-alkoxycarbonylmethoxy, carbamoyl, sulfamoyl, $(C_1-C_4)$-alkoxysulfonyl, sulfo- and guanidinomethyl, or represents the radical of a 3- to 8-membered monocyclic or 7- to 13-membered bicyclic heterocycle which has at least 1 carbon atom, 1-4 nitrogen atoms and/or 1 sulfur or oxygen atom as ring members and which is optionally substituted by one, two or three identical or different radicals from the series comprising F, Cl, Br, hydroxyl, $(C_1-C_4)$-alkoxy, $(C_1-C_4)$-alkyl, $(C_1-C_4)$-alkoxycarbonyl, amino or trifluoromethyl, and A denotes a radical, which is linked N-terminal via —$NR^6$— with —CO— and C-terminal via —CO— with B, of a natural or unnatural amino acid from the series comprising phenylalanine, histidine, tyrosine, tryptophan, β-2-thienylalanine, β-3-thienylalanine, β-2-furylalanine, β-3-furylalanine, 4-chlorophenylalanine, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, 2-fluorophenylalanine, 3-fluorophenylalanine, 4-fluorophenylalanine, homophenylalanine, DOPA, O-dimethyl-DOPA, 2-amino-4-(2-thienyl)-butyric acid, benzodioxol-5-yl-alanine, N-methyl-histidine,2-amino-4-(3-thienyl)-butyric acid, 2-(2-thienyl)-serine, (Z)-dehydrophenylalanine or (E)-dehydrophenylalanine, and $R^6$ denotes hydrogen, B denotes a radical, which is linked N-terminal via —$NR^7$— with A and C-terminal via —CO— with

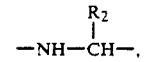

of a natural or unnatural amino acid from the series comprising phenylalanine, histidine, tyrosine, tryptophan, methionine, leucine, isoleucine, asparagine, aspartic acid, β-2-thienylalanine, β-3-thienylalanine, β-2-furylalanine, β-3-furylalanine, lysine, ornithine, valine, alanine, 2,4-diaminobutyric acid, arginine, 4-chlorophenylalanine, methionine sulfone, methionine sulfoxide, 2-pyridylalanine, 3-pyridylalanine, cyclohexylalanine, cyclohexylglycine, im-methylhistidine, O-methyltyrosine, O-benzyltyrosine, O-tert.-butyltyrosine, phenylglycine, 1-naphthylalanine, 2-naphthylalanine, 4-nitrophenylalanine, norvaline, β-2-benzo[b]thienylalanine, β-3-benzo[b]thienylalanine, 2-fluorophenylalanine, 3-fluorophenylalanine, 4-fluorophenylalanine, norleucine, cysteine, S-methylcysteine, 1,2,3,4-tetrahydroisoquinoline-3-carboxylic acid, homophenylalanine, DOPA, O-dimethyl-DOPA, 2-amino-4-(2-thienyl)-butyric acid, benzodioxol-5-yl-alanine, N-methyl-histidine, 2-amino-4-(3-thienyl)-butyric acid, 3-(2-thienyl)-serine, (Z)-dehydrophenylalanine or (E)-dehydrophenylalanine, (1,3-dioxolan-2-yl)-alanine, N-pyrrolylalanine,(1-, 3- or 4-pyrazolyl)-alanine, (4-thiazolyl)alanine, (2-, 4- or 5-pyrimidyl)-alanine, cyclopentylglycine, tert.butylglycine or phenylserine, and $R^7$ denotes hydrogen, and $R^2$ denotes hydrogen, $(C_1-C_5)$-alkyl, $(C_5-C_6)$-cycloalkyl-$C_1-C_4)$-alkyl, $(C_6-C_{10})$-aryl-$(C_1-C_4)$-alkyl or (heterocyclyl)-$(C_1-C_4)$-alkyl, where the heterocycle has 5 or 6 ring members, of which 1 or 2 are sulfur and/or oxygen atoms, $R^3$ denotes hydrogen, $(C_1-C_{10})$-alkyl, $(C_6-C_{14})$-aryl or $(C_6-C_{14})$-aryl-$(C_1-C_4)$-alkyl, X as desired can be absent or represents —O—, —S—, —$CF_2$—, —CO—, or —$CHR^8$—, in which $R^8$ denotes hydrogen, $(C_1-C_7)$-alkyl, $(C_1-C_5)$-alkoxy, $(C_1-C_5)$-alkylthio, $(C_1-C_5)$-alkylamino, —OH, —$N_3$, —F, —Cl, —Br or —I, $R^4$ denotes —OH, —$NH_2$ or a 5- or 6-membered heteroaryl which contains 1 or 2 nitrogen atoms and can partially or completely hydrogenated and is optionally substituted by one, two or three identical or different radicals from the series comprising F, Cl, Br, hydroxyl, $(C_1-C_4)$-alkoxy, $(C_1-C_4)$-alkyl, $(C_1-C_4)$-alkoxycarbonyl, amino or trifluoromethyl, p and q denote, independently of one another, 0, 1, 2, 3 or 4, $R^5$ has the same meaning as $R^1$ or else forms, together with $R^1$ and the nitrogen atom connecting them, a three- to eight-membered monocycle or a seven- to thirteen-membered bicycle which has at least 1 carbon atom, 1–4 nitrogen atoms and/or 1 sulfur or oxygen atom as ring members and which can optionally be substituted by one, two or three identical or different radicals from the series comprising $(C_1-C_6)$-alkyl, hydroxyl, hydroxy-$(C_1-C_6)$-alkyl, $(C_1-C_6)$-alkoxy, $(C_1-C_6)$-alkoxy-$(C_1-C_6)$-alkyl, carboxyl, carboxy-$(C_1-C_6)$-alkyl, $(C_1-C_6)$-alkoxycarbonyl, $(C_1-C_6)$-alkoxycarbonyl-$(C_1-C_6)$-alkyl, halogen, amino, amino-$(C_1-C_6)$-alkyl, $(C_1-C_6)$-alkylamino, $(C_1-C_6)$-alkylamino-$(C_1-C_6)$-alkyl, di-$(C_1-C_6)$-alkylamino or di-$(C_1-C_6)$-alkylamino-$(C_1-C_6)$-alkyl, as well as the physiologically tolerated salts thereof.

Particularly preferred compounds of the formula I are those in which $R^1$ denotes hydrogen, $(C_1-C_{10})$-alkyl, which is optionally substituted by up to three identical or different radicals from the series comprising hydroxyl, carboxyl, amino, $(C_1-C_4)$-alkylamino, di-$(C_1-C_4)$-alkylamino or $(C_1-C_4)$-alkoxycarbonylamino, or phenyl which is optionally substituted by one or two radicals from the series comprising F, Cl, hydroxyl, amino or trifluoromethyl, or phenyl-$(C_1-C_4)$-alkyl in which the phenyl moiety is optionally substituted by one or two identical or different radicals from the series comprising F, Cl, hydroxyl, amino, $(C_1-C_4)$-alkylamino, di-$(C_1-C_4)$-alkylamino, carboxyl, amino-$(C_1-C_4)$-alkyl, $(C_1-C_4)$-alkylamino-$(C_1-C_4)$-alkyl or di-$(C_1-C_4)$-alkylamino-$(C_1-C_4)$-alkyl, A denotes a radical, which is linked N-terminal via —$NR^6$— with —CO—and C-terminal via —CO— with B, of an amino acid from the series comprising phenylalanine, tyrosine, β-2-thienylalanine, β-3-thienylalanine, 4-chlorophenylalanine, O-methyltyrosine, 1-naphthylalanine, 2-naphthylalanine, 2-fluorophenylalanine, 3-fluorophenylalanine or 4-fluorophenylalanine, and $R^6$ denotes hydrogen, B denotes a radical, which is linked N-terminal via —$NR^7$— with A and C-terminal via —CO— with —NH—$CHR^2$—, of an amino acid from the series comprising phenylalanine, histidine, leucine, β-2-thienylalanine, β-3-thienylalanine, lysine, norvaline, 2-fluorophenylalanine, 3-fluorophenylalanine, 4-fluorophenylalanine, norleucine, S-methylcysteine, (1,3-di-oxolan-2-yl)-alanine, (1-, 3- or 4-pyrazolyl)alanine, 4-thiazolylalanine, (2-, 4- or 5-pyrimidyl)-alanine and $R^7$ denotes hydrogen, $R^2$ denotes isobutyl, cyclohexylmethyl, benzyl or (1,3-dithiolan-2-yl)-methyl, $R^3$ denotes hydrogen, X as desired can be absent or represents —S—, —CO— or —$CHR^8$—, in which $R^8$ denotes hydrogen, hydroxyl, $(C_1-C_5)$-alkoxy or fluorine, $R^4$ denotes 2-imidazolyl, 4-imidazolyl, 5-imidazolyl, 2-pyridyl, 3-pyridyl, 4-pyridyl, 2-piperidyl, 3-piperidyl, 4-piperidyl, 1-piperazinyl or 2-piperazinyl, it being possible for the said heterocyclic radicals each to be substituted by one or two identical or different radicals from the series comprising fluorine, methoxy, methyl, ethyl, $(C_1-C_4)$-alkoxycarbonyl, amino or trifluoromethyl, p and q denote, independently of one another, 0, 1 or 2, $R^5$ has the same meaning as $R^1$ or else forms, together with $R^1$ and the nitrogen atom connecting them, a radical from the series comprising pyrrolidinyl, piperidyl, morpholinyl, thiomorpholinyl, piperazinyl, homopiperazinyl or hexahydroazepinyl, it being possible for the said radicals each to be substituted by one or two identical or different substituents from the series comprising methyl, ethyl, propyl, isopropyl, n-butyl, s-butyl, isobutyl, tert.butyl, hydroxyl, hydroxymethyl, hydroxyethyl, methoxy, carboxyl, carboxymethyl, carboxyethyl, methoxycarbonyl, ethoxycarbonyl, $(C_1-C_2)$-alkoxycarbonyl-$(C_1-C_4)$-alkyl, fluorine, chlorine, bromine, amino, amino-$(C_1-C_4)$-alkyl, $(C_1-C_4)$-amino, $(C_1-C_4)$-alkylamino-$(C_1-C_4)$-alkyl, di-$(C_1-C_4)$-alkylamino or di-$(C_1-C_4)$-alkylamino-$(C_1-C_4)$-alkyl, as well as the physiologically tolerated salts thereof.

The compounds of the formula I can be prepared by reacting a compound of the formula II

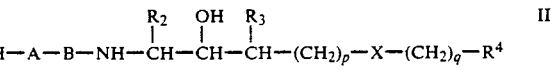

$$H-A-B-NH-\underset{\underset{R_2}{|}}{CH}-\underset{\underset{OH}{|}}{CH}-\underset{\underset{R_3}{|}}{CH}-(CH_2)_p-X-(CH_2)_q-R^4 \quad \text{II}$$

in which $R^2$, $R^3$, $R^4$, A, B, X, p and q have the same meaning as in formula I, in succession, firstly with a carbonic acid derivative of the formula III

$$\underset{R_9-\overset{\overset{O}{\|}}{C}-R^{10}}{} \quad \text{(III)}$$

in which $R^9$ and $R^{10}$ denote, identically or differently and independently of one another, halogen, $(C_1-C_7)$-alkoxy, $(C_6-C_{12})$-aryloxy, $(C_1-C_7)$-alkylthio, $(C_6-C_{12})$-arylthio or a radical Het- or Het-O-, it being possible for Het to be a mono- or bicyclic heterocycle, or in which $R^9$ and $R^{10}$ belong, together with the C=O group, to a mono- or bicyclic heterocycle of the type

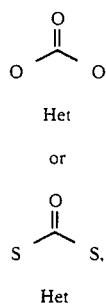

or

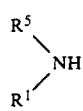

and subsequently with an amine of the general formula IV $$R^5\!\!\diagdown_{\!\!NH}\diagup\!\!R^1 \quad (IV)$$

in which $R^1$ and $R^5$ have the same meaning as in formula I, where appropriate eliminating again temporarily introduced protective groups and, where appropriate, converting the compound obtained in this way into the physiologically tolerated salt thereof.

The formula III preferably represents phosgene, 1,1'-carbonyldiimidazole, 1,1'-carbonyldi-(1,2,4)-triazole, di-(N-succinimidyl) carbonate, di-(1-benzotriazolyl) carbonate, N,N'-carbonyl-bis-(2-methylimidazole) or 4,6-diphenylthieno[3,4-d]-1,3-dioxol-2-one 5,5-dioxide (Steglich reagent).

The reaction is preferably carried out in an inert organic solvent such as, for example, toluene, methylene chloride, chloroform, tetrahydrofuran, dimethylformamide or acetonitrile.

It is carried out where appropriate in the presence of an auxiliary base such as, for example, potassium carbonate, sodium carbonate, triethylamine, pyridine, 1,5-diazabicyclo-[5.4.0]-undec-5-ene or 1,5-diazabicyclo-[4.3.0]-non-5-ene. Pyridine is preferred.

The temperatures can be, for example between $-80°$ C. and the boiling point of the particular solvent, but are preferably between $-80°$ C. an $+50°$ C.

The compounds of the formula I can also be obtained by coupling a fragment with a terminal carboxyl group, or the reactive derivative thereof, with a corresponding fragment with a free amino group, where appropriate eliminating (a) protective group(s) temporarily introduced to protect other functional groups, and converting the compound obtained in this way into the physiologically tolerated salt thereof where appropriate. The compounds of the formula II are obtained from compounds of the formula V

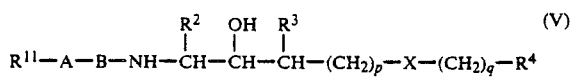

in which $R^2$, $R^3$, $R^4$, A, B, X, p and q have the same meaning as in formula I, and in which R: denotes an amino-protective group which can easily be eliminated, preferably tert.butyloxycarbonyl or benzyloxycarbonyl, by elimination of this protective group under the customary conditions, for example by acid or alkaline hydrolysis or hydrogenolysis, where appropriate with temporary protection of the hydroxyl functionality.

The compounds of the formulae III and IV are known from the literature, and most of them can be bought. The compounds of the formula V are disclosed in European Patent Application 255 082 or can be obtained in an analogous manner from the appropriate starting materials.

Fragments of a compound of the formula I with a terminal carboxyl group have the following formulae VIa)-VIb):

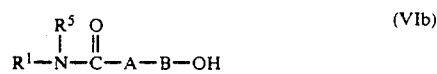

in which $R^1$, $R^5$, A and B have the same meaning as in formula I.

Fragments of a compound of the formula I with a terminal amino group have the following formulae VIIa)-VIIb):

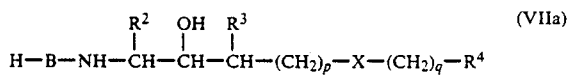

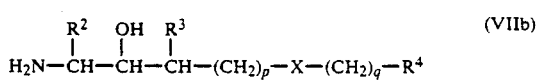

in which $R^2$, $R^3$, $R^4$, B, X, p and q have the same meaning as in formula I.

Methods suitable for the preparation of an amide linkage are described, for example, in Houben-Weyl, Methoden der organischen Chemie (Methods of Organic Chemistry), volume 15/2; Bodanszky et al., Peptide Synthesis, 2nd ed. (Wiley & Sons, New York 1976) or Gross, Meienhofer, The Peptides: Analysis, synthesis, biology (Academic Press, New York 1979). The following methods are preferably employed: active ester method with N-hydroxy-succinimide as ester component, coupling with a carbodiimide such as dicyclohexylcarbodiimide or with propanephosphonic anhydride and the mixed anhydride method with pivaloyl chloride.

The preparation of the optically active amines of the formula VIIb used as starting compounds starts from optically active α-amino acids, with retention of the center of asymmetry thereof. For this purpose, an N-protected amino aldehyde is prepared in a known manner and is coupled in an aldol-analogous addition to an appropriate heteroarylalkyl building block and, after elimination of the N-protective group, yields amino alcohols of the formula VIIb). As an alternative to this, the epoxides are prepared in a manner known per se from the protected amino aldehydes via the allylamines. Either the epoxides can be reacted directly with the appropriate arylalkyl nucleophiles, or the epoxide is initially opened with trimethylsilyl chloride and NaI in acetonitrile, the silyl ether is cleaved with CsF, and the iodide is protected with 2,2-dimethoxypropane under acid catalysis as the oxazolidine. This iodide can be reacted with less reactive nucleophiles. The synthesis of arylalkyl-substituted amino alcohols extended by one $CH_2$ group starts, for example, from Boc-ACHPA-OEt (prepared as described in J. Med. Chem. 28, 1779 (1985)). Initial N,O protection is followed by reduction of the ester functionality and finally conversion of the hydroxyl functionality into a bromide, which can be reacted with arylalkyl nucleophiles under analogous conditions as the already mentioned electrophiles. Examples of suitable arylalkyl nucleophiles are acetylimines and acetylhydrazones. Further compounds of the arylalkyl-substituted amino alcohols with extended $CH_2$ group(s) can be obtained by the generally customary methods for chain extension. If the chosen synthetic route results in diastereomers with respect to the center carrying the OH, these can be separated in a manner known per se, for example by fractional crystallization or by chromatography. The diastereomeric purity is checked using HPLC, and the enantiomeric purity can be checked in a known manner by conversion into Mosher derivatives (H. S. Mosher et al., J. org. Chem. 34. 2543 (1969)).

N-protected amino aldehydes are prepared as described by B. Castro et al. (Synthesis 1983, 676).

The addition of the arylalkyl nucleophiles onto the said N-protected electrophiles (preferably N-tert.-butoxycarbonyl and benzyloxycarbonyl protective groups is carried out in a solvent which is inert towards bases, such as ether, THF, toluene, DMF, DMSO or dimethoxyethane.

Bases which can be used for the deprotonation of the heteroarylalkyl component are alkali metal alcoholates such as potassium O-tert.-butylate, sodium methylate, alkali metal hydrides such as sodium or potassium hydride, organometallic bases such as n-butyllithium, s-butyllithium, methyllithium or phenyllithium, sodamide as well as alkali metal salts of organic nitrogen bases such as lithium diisopropylamide.

Operations required before and after the preparation of compounds of formula I, such as the introduction and elimination of protective groups, are known from the literature and described, for example, in T. W. Greene, "Protective Groups in Organic Synthesis". Salts of compounds of the formula I with salt-forming groups are prepared in a manner known per se, by, for example, reacting a compound of the formula I with a basic group with a stoichiometric amount of a suitable acid. Mixtures of stereoisomers, especially mixtures of diastereomers, which are produced when racemic amino acids A and B are used, can be separated in a manner known per se by fractional crystallization or by chromatography.

The compounds of the formula I according to the invention show enzyme-inhibiting properties, in particular they inhibit aspartyl proteases such as renin and viral proteases such as HIV protease.

Renin is a proteolytic enzyme from the class of aspartyl proteases which is secreted as a consequence of various stimuli (volume depletion, sodium deficiency, β-receptor stimulation) from the juxtaglomerular cells of the kidney into the blood circulation. There it eliminates the decapeptide angiotensin I from the angiotensinogen which is secreted by the liver. This decapeptide is converted by angiotensin converting enzyme (ACE) into angiotensin II. Angiotensin II plays an essential part in the regulation of blood pressure, because it raises the blood pressure directly by vasoconstriction. In addition, it stimulates the secretion of aldosterone from the adrenal and, in this way, via inhibition of sodium excretion, increases the extracellular fluid volume, which in turn contributes to raising the blood pressure. Inhibitors of the enzymatic activity of renin bring about a reduced formation of angiotensin I, the consequence of which is a reduced formation of angiotensin II. The lowering of the concentration of this active peptide hormone is the direct cause of the action of renin inhibitors to lower blood pressure.

The activity of renin inhibitors can be examined by in vitro tests. These entail measurement of the reduction in the formation of angiotensin I in various systems (human plasma, purified human renin).

1. Principle of the test

For example human plasma which contains both renin and angiotensinogen is incubated at 37° C. with the compound to be tested. During this, angiotensin I is liberated from angiotensinogen under the action of renin and can subsequently be measured with a commercially available radioimmunoassay. This angiotensin liberation is inhibited by renin inhibitors.

2. Obtaining the plasma

The blood is obtained from volunteer subjects (about 0.5 l per person; Bluko sampler supplied by ASID Bonz und Sohn, Unterschleissheim) and collected in partially evacuated bottles while cooling in ice. Coagulation is prevented by addition of EDTA (final concentration 10 mM). After centrifugation (HS 4 (Sorvall) rotor, 3,500 rpm, 0°–4° C., 15 min; repeat if necessary) the plasma is cautiously removed by a pipette and frozen in suitable portions at −30° C. Only plasmas with sufficiently high renin activity are used for the test. Plasmas with low renin activity are activated by a cold treatment (−4° C., 3 days) (prorenin→renin).

3. Test procedure

Angiotensin I is determined using the Renin-Maia ® kit (Serono Diagnostics S.A., Coinsins, Switzerland). The plasma is incubated in accordance with the instructions given therein:

| Incubation mixture: | 1000 µl of plasma (thawed at 0–4° C.) |
|---|---|
| | 100 µl of phosphate buffer (pH 7.4) |
| | (addition of $10^{-4}$ M ramiprilat) |
| | 10 µl of PMSF solution |
| | 10 µl of 0.1% Genapol PFIC |
| | 12 µl of DMSO or test product |

The test products are generally made into a $10^{-2}$ M solution in 100% dimethyl sulfoxide (DMSO) and diluted appropriately with DMSO; the incubation mixture contains a maximum of 1% DMSO.

The mixtures are mixed in ice and, for the incubation, placed in a water bath (37° C.) for 1 hour. A total of 6 samples (100 µl each) are taken from an additional mixture without inhibitor and without further incubation for determination of the initial angiotensin I content of the plasma used.

The concentrations of the test products are chosen such that the range of 10–90% enzyme inhibition is approximately covered (at least five concentrations). At the end of the incubation time, three 100 µl samples from each mixture are frozen in precooled Eppendorf tubes on dry ice and stored at about −25° C. for the angiotensin I determination (mean from three separate samples).

Angiotensin I radioimmunoassay (RIA)

The instructions for use of the RIA kit (Renin-Maia® kit, Serono Diagnostics S.A., Coinsins, Switzerland) are followed exactly The calibration plot covers the range from 0.2 to 25.0 ng of angiotensin I per ml. The baseline angiotensin I content of the plasma is subtracted from all the measurements. The plasma renin activity (PRA) is reported as ng of ang I/ml ×hour. PRA values in the presence of the test substances are related to a mixture without inhibitor (=100%) and reported as % activity remaining. The $IC_{50}$ value is read off from the plot of % activity remaining against the concentration (M) of the test product (logarithmic scale).

The compounds of the general formula I described in the present invention show inhibitory actions at concentrations of about $10^{-5}$ to $10^{-10}$ mol/l in the in vitro test.

Renin inhibitors bring about a lowering of blood pressure in salt-depleted animals. Because human renin differs from the renin of other species, primates such as, for example Rhesus monkeys are employed in the in vivo test of renin inhibitors. Primate renin and human renin have substantially homologous sequences. Endogenous renin release is stimulated by i.v. injection of furosemide. The test compounds are subsequently administered and their action on the blood pressure and heart rate is measured. The compounds of the present invention are active in this test in a dose range of about 0.1–5 mg/kg i.v. and on intraduodenal administration by gastroscope in the dose range of about 1–50 mg/kg. The compounds of the general formula I described in the present invention can be used as antihypertensives and for the treatment of heart failure.

HIV protease is cut autocatalytically out of the GAG-POL polypeptide and subsequently cleaves the precursor peptide p55 into the core antigens p17, p24 and p14. It is therefore an essential enzyme, inhibition of which interrupts the lifecycle of the virus and suppresses its growth.

Biological tests showed that the compounds according to the invention have an enzyme-inhibitory action and inhibit viral enzymes such as HIV protease too. The inhibiting action on HIV protease is particularly important and qualifies the compounds according to the invention, in particular, for the therapy and prophylaxis of diseases caused by infection with HIV. The compounds of the general formula I according to the invention show inhibitory actions at concentrations of about $10^{-4}$ to $10^{-8}$ mol/l in the in vitro tests used.

The invention furthermore relates to the use of compounds of the formula I for the preparation of pharmaceuticals for the therapy of high blood pressure and the treatment of congestive heart failure and for the therapy and prophylaxis of virus diseases, especially of diseases caused by HIV, as well as to the said pharmaceuticals.

Pharmaceutical products contain an effective amount of the active substance of the formula I together with an inorganic or organic excipient which can be used in pharmacy. Intranasal, intravenous, subcutaneous or oral use is possible. The dosage of the active substance depends on the warm-blooded species, the body weight, age and the mode of administration.

The pharmaceutical products of the present invention are prepared in dissolving, mixing, granulating or coating processes known per se.

For a form for oral use, the active compounds are mixed with the additives customary for this purpose, such as excipients. stabilizers or inert diluents, and converted by customary methods into suitable dosage forms such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, potassium phosphate. lactose, glucose, magnesium stearyl fumarate or starch, especially corn starch. This preparation can be carried out both as dry and wet granules. Examples of suitable oily excipients or solvents are vegetable or animal oils, such as sunflower oil and fish liver oil.

For subcutaneous or intravenous administration. the active compounds, or the physiologically tolerated salts thereof, are converted into solutions, suspensions or emulsions, if desired with the substances customary for this purpose, such as solubilizers, emulsifiers or other auxiliaries. Examples of suitable solvents are: water, physiological sodium chloride solutions or alcohols, for example ethanol, propanediol or glycerol, as well as sugar solutions such as glucose or mannitol solutions, or else a mixture of the various solvents mentioned.

| List of abbreviations used: | |
|---|---|
| Boc | tert.-Butoxycarbonyl |
| TLC | Thin-layer chromatography |
| DCC | Dicyclohexylcarbodiimide |
| DCI | Desorption Chemical Ionization |
| DNP | 2,4-Dinitrophenyl |
| EI | Electron Impact |
| FAB | Fast atom bombardment |
| HOBt | 1-Hydroxybenzotriazole |
| M | Molecular peak |
| MeOH | Methanol |
| MS | Mass spectrum |
| R.T. | Room temperature |
| M.p. | Melting point |
| Thi | β-2-Thienylalanine |

The other abbreviations used for amino acids correspond to the three-letter code customary in peptide chemistry, as is described, for example, in Eur. J. Biochem. 138, 9–37 (1984). Unless expressly indicated otherwise, the amino acids are always in the L configuration.

The examples which follow serve to illustrate the present invention without restricting it thereto.

EXAMPLE 1

1-Cyclohexyl-6-(2-pyridyl)-2S-[N-[N-(piperazin-1-ylcarbonyl)-L-phenylalanyl-L-norvalyl]amino]-3S-hexanol 1a) Boc-Phe-Nva-OMe 15.0 g (0.056 mol) of Boc-Phe-OH and 9.4 g (0.056 mol) of Nva-OMe hydrochloride are dissolved in 250 ml of absolute methylene chloride. To this are added dropwise, while cooling in ice, first 38.6 ml (0.28 mol) of absolute triethylamine and then 36.4 ml of propanephosphonic anhydride (50 % in methylene chloride). The reaction solution is stirred at room temperature for 3 hours and left to stand overnight. To hydrolyze, it is poured onto ice-water and stirred vigorously for 2 hours, and the organic phase is separated off and washed with 10 % strength citric acid solution, saturated sodium bicarbonate solution and water, dried over sodium sulfate and concentrated.

Yield: 20.8 g (98%) of the title compound $R_f$(methylene chloride/MeOH 9:1)=0.69

MS (DCI)=378 (M+1)

1b) Boc-Phe-Nva-OH 20.1 g (0.053 mol) of Boc-Phe-Nva-OMe (Example 1a) are suspended in 30 ml of water and 30 ml of dioxane. 2.5 g (0.106 mol) of lithium hydroxide are introduced at room temperature, and the mixture is stirred at room temperature for 3 hours. The reaction solution is acidified with 10% strength sodium bisulfate solution, and the product is filtered off with suction and stirred with diisopropyl ether.

Yield: 19.1 g (98%)
MS (DCI)=364 (M+1)

1c) 2S-Amino-1-cyclohexyl-6-(2-pyridyl)-3S-hexanol 5 ml of HCl-saturated dimethoxyethane are added dropwise to 214 mg (0.513 mmol) of 3-Boc-4S-cyclohexylmethyl-2,2-dimethyl-5-(3-(2-pyridyl)-propyl)-oxazolidine in 10 ml of dimethoxyethane in an ice bath, and the mixture is stirred at 0° C for one hour and at room temperature for 5 hours. The reaction solution is concentrated in vacuo and evaporated twice more with toluene.

Yield: 179 mg of the title compound as dihydrochloride

1d) 1-Cyclohexyl-6-(2-pyridyl)-2S-[N-(Boc-Phe-Nva)-amino]-3S-hexanol 1.7 g (3.36 mmol) of 2S-amino-1-cyclohexyl-6-(2-pyridyl)-3S-hexanol-dihydrochloride (prepared in analogy to Example 1c) are dissolved in 10 ml of absolute dimethylformamide and, at room temperature, 1.22 g (3.36 mmol) of Boc-Phe-Nva-OH (Example 1b) and 0.9 g of HOBt are successively added. The mixture is then cooled to 4° C. and, at this temperature 2 ml (15.6 mmol) of N-ethylmorpholine and 0.69 g (3.36 mmol) of DCC are added. The reaction mixture is stirred in the ice bath for 1 hour and at R.T. for 5 hours and left to stand for 3 days. The precipitate is filtered off with suction, the filtrate is poured into ice-water, and the mixture is extracted several times with ethyl acetate. The combined organic phases are washed with saturated sodium bicarbonate solution, water and saturated sodium chloride solution, dried and concentrated, and the crude product is purified by column chromatography on silica gel (mobile phase methylene chloride/methanol 100:0, 98:2, 95:5). 0.8 g of the title compound is obtained.

$R_f$(methylene chloride/MeOH 9:1) =0.53
MS (FAB) =623 (M+1)

1e) 1-Cyclohexyl-6-(2-pyridyl)-2S-[N-(H-Phe-Nva)-amino]-3S-hexanol 92 mg of the title compound are obtained as the dihydrochloride from 97 mg of 1-cyclohexyl-6-(2-pyridyl)-2S-[N-(Boc-Phe-Nva)-amino]-3S-hexanol (Example 1d) in analogy to the process indicated in Example 1c).

1f) 1-Cyclohexyl-6-(2-pyridyl)-2S-[N-[N-(piperazin-1-yl-carbonyl)-Phe-Nva]amino]-3S-hexanol A solution of 118 mg (0.16 mmol) of 1-cyclohexyl-6-(2-pyridyl)-2S-[N-(H-Phe-Nva)-amino]-3S-hexanol (Example 1e) in 10 ml of absolute methylene chloride is added dropwise at −75° C. to a solution of 125 mg (0.32 mmol) of di(benzo-triazolyl) carbonate and 26 µl (0.32 mmol) of pyridine in 10 ml of absolute methylene chloride, and the mixture is stirred at this temperature for 2 hours and at R.T. for 1 hour. The solution is then again cooled to −75° C., and 69 mg (0.8 mmol) of piperazine are added. After one hour at −75° C., the mixture is allowed to warm up slowly and is left to stand at R.T. overnight. The reaction solution is concentrated, the residue is taken up in ethyl acetate, the solution is washed with saturated sodium bicarbonate solution, water and saturated sodium chloride solution, dried and concentrated, and the crude product (106 mg) is purified by medium pressure column chromatography on silica gel (mobile phase gradient methylene chloride/MeOh 99:1 to 1:1). 25.7 mg of the title compound are obtained.

$R_5$ (methylene chloride/MeOH 9:1) =0.03
MS (FAB)=635 (M+1)

EXAMPLE 2

1-Cyclohexyl-6-(2-pyridyl)-2S-[N-[N-(morpholinocarbonyl)-L-phenylalanyl-L-norvalyl]amino]-3S-hexanol 56.6 mg of the title compound are obtained from 108 mg (0.17 mmol) of 1-cyclohexyl-6-(2-pyridyl)-2S-[N-(H-Phe-Nva)-amino]-3S-hexanol (Example 1e), 133 mg (0.34 mmol) of di-(benzotriazolyl) carbonate and 74 µl (0.85 mmol) of morpholine in analogy to the process described in Example 1f).

$R_f$(methylene chloride/MeOH 9:1)=0.39
MS (FAB) =636 (M+1)

The following compounds are obtained using suitable starting materials and employing the processes described in Examples 1 to 2.

EXAMPLE 3

1-Cyclohexyl-6-(2-pyridyl)-2S-[N-[N-(dimethylaminocarbonyl)-L-phenylalanyl-L-norvalyl]amino]-3S-hexanol;

MS (FAB)=594 (M+1)

EXAMPLE 4

1-Cyclohexyl-6-(2-pyridyl)-2S-[N-[N-(diethylaminocarbonyl)-L-phenylalanyl-L-norvalyl]amino]-3S-hexanol;

MS (FAB)=622 (M+1)

EXAMPLE 5

1-Cyclohexyl-6-(2-pyridyl)-2S-[N-[N-(4-methylpiperazin-1-yl-carbonyl)-L-phenylalanyl-L-norvalyl]amino]-3S-hexanol;

MS (FAB)=649 (M+1)

EXAMPLE 6

1-Cyclohexyl-6-(2-pyridyl)-2S-[N-[N-(thiomorpholinocarbonyl)-L-phenylalanyl-L-norvalyl]amino]-3S-hexanol;

MS (FAB)=652 (M+1)

EXAMPLE 7

1-Cyclohexyl-6-(2-pyridyl)-2S-[N-[N-(1-piperidylcarbonyl)-L-phenylalanyl-L-norvalyl]amino]-3S-hexanol;

MS (FAB)=634 (M+1)

EXAMPLE 8

1-Cyclohexyl-6-(2-pyridyl)-2S-[N-[N-(4-tert.butyloxy-carbonylpiperazin-1-yl-carbonyl)-L-phenylalanyl-L-norvalyl]-amino]-3S-hexanol;

MS (FAB)=735 (M+1)

EXAMPLE 9

1-Cyclohexyl-6-(2-pyridyl)-2S-[N-[N-(dimethylaminocarbonyl)-L-phenylalanyl-L-histidyl]amino]-3S-hexanol;

MS (FAB)=632 (M+1)

EXAMPLE 10

1-Cyclohexyl-6-(2-pyridyl)-2S-[N-[N-(diethylaminocarbonyl)-L-phenylalanyl-L-histidyl]amino]-3S-hexanol;

MS (FAB)=660 (M+1)

EXAMPLE 11

1-Cyclohexyl-6-(2-pyridyl)-2S-[N-[N-(morpholinocarbonyl)-L-phenylalanyl-L-histidyl]amino]-3S-hexanol;

MS (FAB)=674 (M+1)

EXAMPLE 12

1-Cyclohexyl-6-(2-pyridyl)-2S-[N-[N-(piperazin-1-yl-carbonyl)-L-phenylalanyl-L-histidyl]amino]-3S-hexanol;

MS (FAB)=673 (M+1)

EXAMPLE 13

1-Cyclohexyl-6-(2-pyridyl)-2S-[N-[N-(4-methylpiperazin-1-yl-carbonyl)-L-phenylalanyl-L-histidyl]amino]-3S-hexanol;

MS (FAB)=687 (M+1)

EXAMPLE 14

1-Cyclohexyl-6-(2-pyridyl)-2S-[N-[N-(thiomorpholinocarbonyl)-L-phenylalanyl-L-histidyl]amino]-3S-hexanol;

MS (FAB)=690 (M+1)

EXAMPLE 15

1-Cyclohexyl-6-(2-pyridyl)-2S-[N-[N-(1-piperidylcarbonyl)-L-phenylalanyl-L-histidyl]amino]-3S-hexanol;

MS (FAB)=672 (M+1).

EXAMPLE 16

1-Cyclohexyl-6-(2-pyridyl)-2S-[N-[N-(4-tert.butyloxycarbonylpiperazin-1-yl-carbonyl)-L-phenylalanyl-L-histidyl]amino]-3S-hexanol;

MS (FAB)=773 (M+1)

EXAMPLE 17

1-Cyclohexyl-6-(2-pyridyl)-2S-[N-[N-(morpholinocarbonyl)-L-(β-2-thienylalanyl)-L-norvalyl]amino]-3S-hexanol;

MS (FAB)=642 (M+1)

EXAMPLE 18

1-Cyclohexyl-6-(2-pyridyl)-2S-[N-[N-(piperazin-1-yl-carbonyl)-L-(β-2-thienylalanyl)-L-norvalyl]amino]-3S-hexanol;

MS (FAB)=641 (M+1)

EXAMPLE 19

1-Cyclohexyl-6-(2-pyridyl)-2S-[N-[N-(morpholinocarbonyl)-L-(β-2-thienylalanyl)-L-histidyl]amino]-3S-hexanol;

MS (FAB)=680 (M+1)

EXAMPLE 20

1-Cyclohexyl-6-(2-pyridyl)-2S-[N-[N-(piperazin-1-yl-carbonyl)-L-(β-2-thienylalanyl)-L-histidyl]amino]-3S-hexanol;

MS (FAB)=679 (M+1)

EXAMPLE 21

1-Phenyl-6-(2-pyridyl)-2S-[N-[N-(morpholinocarbonyl)-L-phenylalanyl-L-norvalyl]amino]-3S-hexanol;

MS (FAB)=635 (M+1)

EXAMPLE 22

2-Methyl-8-(2-pyridyl)-4S-[N-[N-(morpholinocarbonyl)-L-phenylalanyl-L-histidyl]amino]-5S-octanol;

MS (FAB)=634 (M+1)

EXAMPLE 23

1-Cyclohexyl-5-fluoro-6-(2-pyridyl)-2S-[N-[N-(morpholinocarbonyl)-L-phenylalanyl-L-norvalyl]amino]-3S-hexanol;

MS (FAB)=654 (M+1)

EXAMPLE 24

1-Cyclohexyl-5-fluoro-6-(2-pyridyl)-2S-[N-[N-(morpholinocarbonyl)-L-phenylalanyl-L-histidyl]amino]-3S-hexanol;

MS (FAB)=692 (M+1)

EXAMPLE 25

1-Cyclohexyl-6-(1-methylimidazol-2-yl)-2S-[N-[N-(morpholinocarbonyl)-L-phenylalanyl-L-norvalyl]amino]-3S-hexanol;

MS (FAB)=641 (M+1)

EXAMPLE 26

1-Cyclohexyl-6-(1-methylimidazol-2-yl)-2S-[N-[N-(morpholinocarbonyl)-L-phenylalanyl-L-histidyl]amino]-3S-hexanol.

MS (FAB)=679 (M+1)

We claim:
1. A compound of the formula I

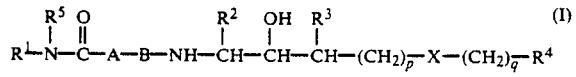

in which

A denotes a radical, which is linked N-terminal via —NR⁶— with —CO— and C-terminal via —CO— with B, of an amino acid selected from the group consisting of phenylalamine, tyrosine, β-2-thienylalanine, β-3-thienylalanine, 4-chlorophenylalanine, O-methylalanine, 1-anphthylalanine, 2-naphthylalanine, 2-fluorophenylalanine, 3-fluorophenylalanine and 4-fluorophenylalanine, and $R^6$ denotes hydrogen, B denotes a radical, which is linked N-terminal via $-NR^7-$ with A and C-terminal via $-CO-$ with $-NH-CHR^2-$, of an amino acid selected from the group consisting of phenylalanine, histidine, leucine, β-2-thienylalanine, β-b 3-thienylalanine, lysine, norvaline, 2-fluorophenylalanine, 3-fluorophenylalanine, 4-fluorophenylalanine, norleucine, S-methylcysteine, (1,3-dioxolan-2-yl)-alanine, (1-, 3- or 4-pyrazolyl)-alanine, 4-thiazolylalanine and (2-, 4- or 5-pyridimidyl)-alanine and $R^7$ denotes hydrogen, $R^2$ denotes hydrogen, $(C_1-C_{10})$-alkyl, $(C_4-C_7)$-cycloalkyl-$(C_1-C_6)$-alkyl or $(C_6-C_{14})$-aryl-$(C_1-C_6)$-alkyl, $R^3$ is hydrogen, X is absent, $R^4$ denotes 2-imidazolyl, 4-imidiazolyl, 5-imidazolyl, 2-pyridyl, 3-pyridyl, 4-pyridyl, 2-piperidyl, 3-piperidyl, 4-piperidyl, 1-piperazinyl or 2-piperazinyl, P is O q denotes 0, 1 or 2

$R^1$ and $R^5$ form together with the nitrogen atom connecting them, a radical selected from the group consisting of pyrrolidinyl, piperidyl, morpholinyl, thiomorpholinyl, piperazinyl, homopiperazinyl and hexahydroazepinyl, which may be substituted by one substituent selected from the group consisting of methyl, ethyl, propyl, isopropyl, n-butyl, s-butyl, isobutyl and tert.butyl, as well as the physiologically tolerated salt thereof.

2. A pharmaceutical composition for the treatment of high blood pressure comprising an effective amount of a compound of the formula I as claimed in claim 1, or a physiologically tolerated salt thereof, and a pharmaceutically acceptable vehicle.

3. A method for the treatment of high blood pressure in a mammal, which comprises administration of an effective amount of a compound of the formula I as claimed in claim 1, or a physiologically tolerated salt thereof to said mammal.

* * * * *

UNITED STATES PATENT AND TRADEMARK OFFICE
CERTIFICATE OF CORRECTION

PATENT NO. : 5,116,835

DATED : May 26, 1992

INVENTOR(S) : Wolfgang Ruger et al.

It is certified that error appears in the above-identified patent and that said Letters Patent is hereby corrected as shown below:

ON THE TITLE PAGE:

Abstract, line 8, change "indpendently" to --independently--.

Claim 1, column 16, line 68, change "phenylalamine" to --phenylalanine--.

Claim 1, column 17, line 2, change "1-anphthylalanine" to --1-naphthylalanine--.

Claim 1, column 17, line 9, change "ß-b 3-thienylalanine" to --ß-3-thienylalanine--.

Claim 1, column 17, lines 13 and 14, change "(2-,4- or 5-pyridimidyl)-alanine" to (2-,4- or 5-pyrimidyl)-alanine--".

UNITED STATES PATENT AND TRADEMARK OFFICE
CERTIFICATE OF CORRECTION

PATENT NO. : 5,116,835

DATED : May 26, 1992

INVENTOR(S) : Wolfgang Ruger et al.

It is certified that error appears in the above-identified patent and that said Letters Patent is hereby corrected as shown below:

Claim 1, column 17, line 20, change "4-imidiazolyl" to --4-imadazolyl--.

Signed and Sealed this

Twenty-first Day of September, 1993

Attest:

BRUCE LEHMAN

Attesting Officer

Commissioner of Patents and Trademarks